United States Patent [19]

McMillan

[11] 4,094,639

[45] June 13, 1978

[54] DEODORIZER

[75] Inventor: Ronald J. McMillan, Fort Lauderdale, Fla.

[73] Assignee: The Raymond Lee Organization, Inc., New York, N.Y. ; a part interest

[21] Appl. No.: 787,775

[22] Filed: Apr. 15, 1977

[51] Int. Cl.² .......................... A61L 3/00; A61L 9/01; A61L 9/04

[52] U.S. Cl. .................................. 21/74 R; 21/122; 239/58; 239/60

[58] Field of Search ............... 21/74 R, 108, 121-127; 239/57, 58, 60; 223/86; 312/31, 31.1, 31.2; 43/125, 126, 131, 132 R

[56] References Cited

U.S. PATENT DOCUMENTS

| 809,662 | 1/1906 | Barnes | 21/108 |
|---|---|---|---|
| 1,016,648 | 2/1912 | Snell | 21/108 |
| 2,545,160 | 3/1951 | Miller | 21/108 |
| 2,763,395 | 9/1956 | Meek | 239/58 |
| 2,797,844 | 7/1957 | Meek | 239/60 |
| 3,098,703 | 7/1963 | Snyder et al. | 21/108 |
| 3,148,808 | 9/1964 | Griffin et al. | 223/86 |
| 3,797,742 | 3/1974 | Clark et al. | 239/60 |

FOREIGN PATENT DOCUMENTS

| 1,064,591 | 5/1954 | France | 239/57 |
|---|---|---|---|
| 401,383 | 11/1933 | United Kingdom | 21/108 |

*Primary Examiner*—Morris O. Wolk
*Assistant Examiner*—Bradley Garris
*Attorney, Agent, or Firm*—Daniel Jay Tick

[57] ABSTRACT

An elongated perforated cylindrical housing sleeve is partitioned at its center thereby dividing the sleeve into a pair of separate equally dimensioned chambers. A pair of deodorizing units are mounted in the housing sleeve each in a corresponding one of the chambers thereof. A pair of cover caps are threadedly coupled to the housing sleeve at corresponding ends thereof for facilitating replacement of deodorizing units in the chambers. The sleeve is mounted on a supporting surface. A cylindrical cover sleeve having a length equal to half the length of the housing sleeve is slidably mounted on the housing sleeve. Thus, the cover sleeve covers one of the chambers of the housing sleeve while freeing the other so that the deodorizing unit in the one of the chambers is preserved while the deodorizing unit in the other of the chambers deodorizes the surrounding area.

1 Claim, 3 Drawing Figures

DEODORIZER

BACKGROUND OF THE INVENTION

The present invention relates to a deodorizer.

Objects of the invention are to provide a deodorizer of simple structure, which is inexpensive in manufacture, installed with facility and convenience, used with facility and convenience, and functions efficiently, effectively and reliably to provide a deodorizer at all times, with a second deodorizer available for instant use upon dissipation of the first.

BRIEF DESCRIPTION OF THE DRAWINGS

In order that the invention may be readily carried into effect, it will now be described with reference to the accompanying drawings, wherein.

Figure 2:
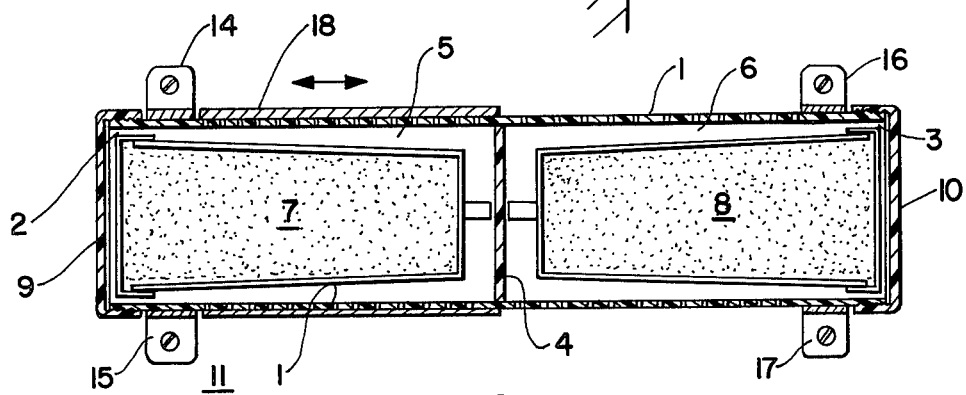
FIG. 2 is a view, on an enlarged scale, partly in section, of the embodiment of FIG. 1.

DETAILED DESCRIPTION OF THE INVENTION:

The deodorizer of the invention comprises an elongated perforated cylindrical housing sleeve 1 having spaced opposite first and second ends 2 and 3, respectively (FIG. 2). A partition 4 is provided at the center of the housing sleeve 1 equidistant from the ends 2 and 3 and dividing the housing sleeve into a pair of separate equally dimensioned chambers 5 and 6, as shown in FIG. 2.

A pair of deodorizing units 7 and 8 are mounted in the housing sleeve 1, as shown in FIG. 2. The deodorizing unit 7 is mounted in the chamber 5 and the deodorizing unit 8 is mounted in the chamber 6 of the housing sleeve 1, as shown in FIG. 2. The deodorizing units comprise any suitable commercially available deodorizing units.

A pair of cover caps 9 and 10 (FIGS. 1 and 2) are threadedly coupled to the housing sleeve 1 at the ends 2 and 3 thereof, respectively, for facilitating replacement of deodorizing units 7 and 8 in the chambers 5 and 6, respectively.

A mounting device of any suitable type mounts the housing sleeve 1 on a supporting surface 11. The housing sleeve 1 is preferably mounted with its axis extending horizontally. The mounting device comprises, in the illustrated embodiment of the invention, a pair of spaced C-shaped brackets 12 and 13. The brackets 12 and 13 have fastening parts 14 and 15, and 16 and 17, respectively (FIG. 2), extending at substantially right angles thereto to permit said brackets to be affixed to the supporting surface 11. The brackets 12 and 13 may be affixed to the supporting surface 11, via their fastening parts by means of magnets or by screws, nails, or the like, when bores are formed through said fastening parts.

Figure 1:
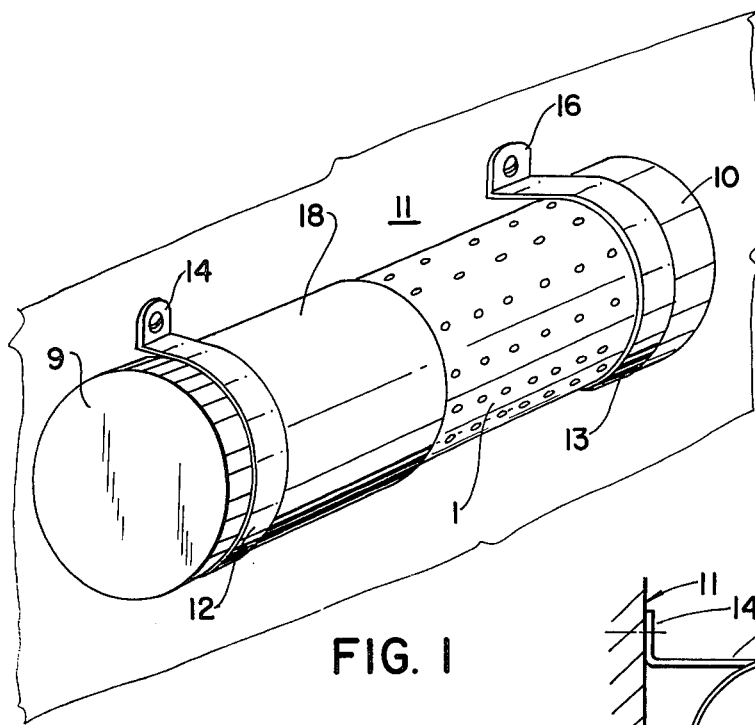
FIG. 1 is a perspective view of an embodiment of the deodorizer of the invention.
Figure 3:
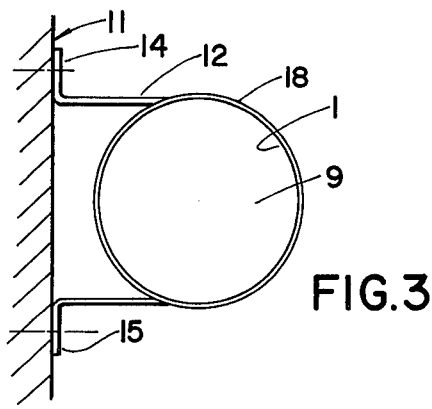
FIG. 3 is an axial view of the embodiment of FIG. 1.

A cylindrical cover sleeve 18 has a length equal to substantially half the length of the housing sleeve 1 and is slidably mounted on said housing sleeve, as shown in FIGS. 1 and 2. The cover sleeve 18 is slidably mounted on the housing sleeve 1 in a manner whereby said cover sleeve covers one of the chambers 5 or 6 of the housing sleeve while freeing the other of said chambers. Thus, the deodorizing unit such as, for example, the deodorizing unit 7 in the one of the chambers such as, for example, the chamber 5, is preserved while the deodorizing unit 8 in the other of the chambers 6 deodorizes the surrounding area, as shown in FIGS. 1 and 2.

Upon dissipation of the deodorizing unit 8, the cover sleeve 18 is moved to cover the chamber 6 thereby providing the fresh deodorizing unit 7 for deodorizing the surrounding area.

While the invention has been described by means of a specific example and in a specific embodiment, I do not wish to be limited thereto, for obvious modifications will occur to those skilled in the art without departing from the spirit and scope of the invention.

I claim:

1. A deodorizer, comprising an elongated perforated cylindrical housing sleeve having spaced opposite first and second ends with a partition at the center thereof equidistant from the ends dividing the housing sleeve into a pair of separate equally dimensioned chambers;

a pair of deodorizing units mounted in the housing sleeve, each in a corresponding one of the chambers thereof;

a pair of cover caps each threadedly coupled to the housing sleeve at a corresponding end thereof for facilitating replacement of deodorizing units in the chambers;

mounting means for mounting the housing sleeve on a supporting surface; and a cylindrical cover sleeve having a length equal to substantially half the length of the housing sleeve and slidably mounted on said housing sleeve in a manner whereby said cover sleeve covers one of the chambers of the housing sleeve while freeing the other so that the deodorizing unit in the one of the chambers is preserved while the deodorizing unit in the other of the chambers deodorizes the surrounding area, said cover sleeve being freely slidable on said housing sleeve for selectively varying the strength of deodorant transmitted from said housing sleeve.

* * * * *